US006492532B2

(12) United States Patent
Utsunomiya et al.

(10) Patent No.: US 6,492,532 B2
(45) Date of Patent: Dec. 10, 2002

(54) METHOD FOR PRODUCING CARBONYL COMPOUND BY DEHYDROGENATING ALCOHOL

(75) Inventors: Masaru Utsunomiya, Okayama (JP); Kazunari Takahashi, Okayama (JP); Yoko Seto, Okayama (JP); Souichi Orita, Okayama (JP); Souichi Amano, Okayama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/933,070

(22) Filed: Aug. 21, 2001

(65) Prior Publication Data

US 2002/0002289 A1 Jan. 3, 2002

Related U.S. Application Data

(63) Continuation of application No. PCT/JP00/08926, filed on Dec. 15, 2000.

(30) Foreign Application Priority Data

Dec. 21, 1999 (JP) ............................................ 11-362393

(51) Int. Cl.[7] .................. C07D 207/267; C07D 307/30; C07D 307/32
(52) U.S. Cl. ........................ 548/554; 549/273; 549/295
(58) Field of Search ........................... 548/554; 549/273, 549/295

(56) References Cited

U.S. PATENT DOCUMENTS 5,106,995 A * 4/1992 Plotkin ........................ 549/273

FOREIGN PATENT DOCUMENTS

| JP | 1-190667 | 7/1989 |
| JP | 11-135374 | 5/1999 |

OTHER PUBLICATIONS

Otake et al., Chemical Abstracts, 112:98377, 1990.*
Ue et al., Chemical Abstracts, 130:360229, 1999.*
Murahashi et al., Journal of Organic Chemistry, "Ruthenium–Catalyzed Oxidative Transformation of Alcohols and Aldehydes to Esters and Lactones", 52(19), 4319–4327, 1987.*
Y. Ishii, et al., "Ruthenium Complex Catalyzed Regioselective Dehydrogenation of Unsymmetrical α,ω–Diols", J. Org. Chem., vol. 51, pp. 2034–2039, 1986.

* cited by examiner

Primary Examiner—Fiona T. Powers
(74) Attorney, Agent, or Firm—Oblon, Spivak, McClelland, Maier & Neustadt, P.C.

(57) ABSTRACT

The present invention provides a method for producing a carbonyl compound by dehydrogenating an alcohol. Namely, it relates to a method for producing a carbonyl compound, which comprises dehydrogenating an alcohol in the presence of a complex compound catalyst comprising ruthenium and an organic phosphine wherein aliphatic carbons are bonded to two or more of the three bonding hands of the phosphorus atom.

10 Claims, No Drawings

METHOD FOR PRODUCING CARBONYL COMPOUND BY DEHYDROGENATING ALCOHOL

This application is a continuation of PCT/JP00/08926 filed Dec. 15, 2000.

TECHNICAL FIELD

The present invention relates to a method for producing a carbonyl compound by dehydrogenating an alcohol. More particularly, it relates to a method for producing a carbonyl compound by dehydrogenating an alcohol in the presence of a complex compound catalyst comprising ruthenium and a specific organic phosphine. A suitable example to which the method of the invention is applied is production of γ-butyrolactone from 1,4-butanediol.

BACKGROUND ART

Hitherto, there have been proposed several methods for producing a carbonyl compound by dehydrogenating an alcohol in the presence of a complex compound catalyst wherein a specific transition metal and a specific organic phosphine are combined. For example, a reaction of obtaining a lactone compound by dehydrogenating a diol using iridium-triisopropylphosphine complex, ruthenium-triphenylphosphine complex and rhenium-triisopropylphosphine complex as catalysts is described in J. Orgmet. Chem., 429 (1992) 269–274, a reaction of obtaining a lactone compound by dehydrogenating a diol using ruthenium-triphenylphosphine complex different from the above as a catalyst is described in J. Org. Chem., 1987, 52, 4319–4327 and Tetrahedron Let., 1981, 22, 5327–5330, and a reaction of obtaining a lactone compound by dehydrogenating a diol using ruthenium-bis(diphenylphosphino) butane compound complex as a catalyst is described in Chem. Soc. Japan, 1982, 1179–1182.

However, in these reactions, the dehydrogenation of the alcohol substrate is accelerated by the presence of a hydrogen acceptor such as acetone in the reaction system, and the catalyst activity is remarkably decreased when the hydrogen acceptor is not present.

In Bull. Chem. Soc. Jpn., 61, 2291–2294 (1988), a reaction of dehydrogenating methanol using rutheniumethyldiphenylphosphine complex or ruthenium-diethylphenylphosphine complex as a catalyst is described. In this method, however, there is a problem that the catalyst activity is remarkably low. In addition, there is no description or no suggestion of a method for producing γ-butyrolactone effectively by the dehydrogenation of 1,4-butanediol and successive intramolecular cyclization.

The reaction requiring a large amount of the hydrogen acceptor is extremely disadvantageous for industrial practice. In addition, since the hydrogen acceptor is converted to other compound through the dehydrogenation of the alcohol, the acceptor cannot be reused. Therefore, the method is regarded to be industrially impractical.

Moreover, there are described methods for producing γ-butyrolactone by dehydrogenating 1,4-butanediol in a vapor phase using copper-chromiummanganese catalyst or copper-chromium-zinc catalyst in Japanese Patent Publication No. 17954/1992 or using a catalyst containing copper, chromium and barium in Japanese Patent Laid-Open No. 232874/1991. These methods, however, do not solve the problems of selectivity and deterioration of the catalysts, or, owing to the vapor phase process, it is difficult to avoid the limitation derived from the equilibrium with the reverse reaction and the problems of the selectivity and the deterioration of the catalyst can be not completely solved.

An object of the invention is to provide a method for producing a carbonyl compound by dehydrogenating an alcohol, wherein the carbonyl compound is produced industrially advantageously at a good selectivity in high yields under mild reaction conditions.

Furthermore, another object of the invention is to provide a method for producing γ-butyrolactone industrially advantageously at a good selectivity in high yields under mild reaction conditions by dehydrogenation of 1,4-butanediol and successive cyclization.

DISCLOSURE OF THE INVENTION

As a result of the extensive studies for solving the above problems, the present inventors have found that a complex compound catalyst comprising ruthenium and an organic phosphine wherein aliphatic carbons are bonded to two or more of the three bonding hands of the phosphorus atom can be used as a catalyst for efficiently dehydrogenating an alcohol to produce a carbonyl compound. Especially, they have found that the above complex compound catalyst can be used as a suitable catalyst for producing γ-butyrolactone from 1,4-butanediol. The invention has been accomplished based on the above findings.

Namely, a gist of the invention is a method for producing a carbonyl compound, which comprises dehydrogenating an alcohol in the presence of a complex compound catalyst comprising ruthenium and an organic phosphine wherein aliphatic carbons are bonded to two or more of the three bonding hands of the phosphorus atom.

Moreover, another gist of the invention is a method for producing γ-butyrolactone, which comprises dehydrogenating 1,4-butanediol in the presence of a complex compound catalyst comprising ruthenium and an organic phosphine wherein aliphatic carbons are bonded to two or more of the three bonding hands of the phosphorus atom.

Best Mode for Carrying Out the Invention

The catalyst for use in the invention is a complex compound catalyst comprising ruthenium and an organic phosphine wherein aliphatic carbons are bonded to two or more of the three bonding hands of the phosphorus atom. The catalyst may be prepared beforehand and used for the reaction, or each component constituting the catalyst may be incorporated into the reaction system to form the catalyst in the reaction system.

The form of ruthenium metal to be fed is not particularly limited and may be metal ruthenium or a ruthenium compound. Examples of the ruthenium compound include oxides, hydroxides, inorganic acid salts, organic acid salts, complex compounds, and the like, and specific examples include ruthenium dioxide, ruthenium tetraoxide, ruthenium hydroxide, ruthenium chloride, ruthenium bromide, ruthenium iodide, ruthenium nitrate, ruthenium acetate, tris(acetylacetonato)ruthenium, sodium hexachlororuthenate, dipotassium tetracarbonylruthenate, pentacarbonylruthenium, cyclopentadienyldicarbonylruthenium, dibromotricarbonylruthenium, chlorotris(triphenylphosphine)hydridoruthenium, tetra(triphenylphophine)dihydridoruthenium, tetra(trimethylphophine)dihydridoruthenium, bis(tri-n-butylphosphine)tricarbonylruthenium, tetrahydridododecacarbonyltetraruthenium, dodecacarbonyltriruthenium, dicesium octadecacarbonylhexaruthenate, tetraphenylphosphonium undecacarbonyl hydridotriruthenate, and the like. Commercially available compounds may be used as these compounds, or they may be synthesized according to known methods.

The organic phosphine for use in the invention is a phosphine wherein aliphatic carbons are bonded to two or more of the three bonding hands of the phosphorus atom. Examples of the organic phosphine include a trialkylphosphine wherein alkyl groups are bonded to all the three bonding hands of the phosphorus atom, a dialkylarylphosphine wherein alkyl groups are bonded to two of the three bonding hands of the phosphorus atom and an aryl group is bonded to the remaining one hand, and the like. One or two or more phosphorus atom(s) may be present in one molecule of the organic phosphine, and the phosphorous atom may be monodentate or polydentate toward ruthenium.

The alkyl group is a saturated or unsaturated, linear, branched chain or cyclic aliphatic hydrocarbon having 1 to 30 carbon atoms, preferably 1 to 20 carbon atoms, more preferably 1 to 10 carbon atoms, which may be substituted. The substituent of the alkyl group is not particularly limited but, for example, an aromatic hydrocarbon such as phenyl, tolyl, and the like may be mentioned. Specific examples of such alkyl group include methyl, ethyl, n-propyl, i-propyl, n-butyl, i-butyl, n-pentyl, n-hexyl, 2-methylpentyl, 2-ethylbutyl, cyclohexyl, n-heptyl, n-octyl, n-nonyl, n-decanyl, benzyl, and the like.

The aryl group is an aromatic hydrocarbon having 1 to 20 carbon atoms, preferably 1 to 10 carbon atoms, which may be substituted. The substituent of the aromatic hydrocarbon includes alkyl groups such as methyl, ethyl, n-propyl, i-propyl, n-butyl, i-butyl, etc.; alkoxy groups such as methoxy, ethoxy, etc.; halogen atoms such as chlorine, bromine, etc.; nitro group; sulfone groups; and the like. Specific examples of such aryl group include phenyl, o-, m-, p-tolyl, o-, m-, p-methoxyphenyl, n-, sec-, tert-butyl, o-, m-, p-chlorophenyl, naphthyl, and the like.

In addition, two or more alkyl groups may be combined to form an alkylene group.

In the organic phosphine of the invention, the above functional groups bonded to the phosphorus atom may be the same or different and any two or three groups may form a ring structure. Moreover, the carbon bonded to the phosphorus group may be primary or secondary, but preferably primary.

Examples of the trialkylphosphine having the above alkyl groups include trialkylphosphines having one phosphorus atom in one molecule such as tri(n-decanyl)phosphine, tri(n-nonyl)phosphine, tri(n-octyl)phosphine, tri(n-heptyl) phosphine, tri(n-hexyl)phosphine, tricyclohexylphosphine, tri(n-pentyl)phosphine, tri(n-butyl)phosphine, tri(i-butyl) phosphine, tri(n-propyl)phosphine, tri(i-propyl)phosphine, triethylphosphine, trimethylphosphine, dimethyl(n-octyl) phosphine, di(n-octyl)methylphosphine, dimethyl(n-heptyl) phosphine, di(n-heptyl)methylphosphine, dimethyl(n-hexyl) phosphine, di(n-hexyl)methylphosphine, dimethylcyclohexylphosphine, dicyclohexylmethylphosphine, dimethylbutylphosphine, di(n-butyl)methylphosphine, tribenzylphosphine, etc.; trialkylphosphines having two or more phosphorus atoms in one molecule such as 1,1,2,2-tetrakis(dimethylphosphino) ethane, 1,1,2,2-tetrakis(dimethylphosphino)propane, 1,1,2, 2-tetrakis(dimethylphosphino)butane, 1,1,2,2-tetrakis (dioctylphosphino)ethane, 1,1,2,2 tetrakis (dioctylphosphino)propane, 1,1,2,2-tetrakis (dioctylphosphino)butane, 1,1,2,2-tetrakis(dihexyl phosphino)ethane, 1,1,2,2-tetrakis(dihexylphosphino) propane, 1,1,2,2-tetrakis(dihexylphosphino)butane, 1,1,2,2-tetrakis(dibutylphosphino)ethane, 1,1,2,2-tetrakis (dibutylphosphino)propane, 1,1,2,2-tetrakis (dibutylphosphino)butane, etc.; phosphines wherein phosphorus atom(s) is ring-forming element(s), such as 1,1-diphosphinane, 1,4-dimethyl-1,4-diphosphinophane, 1,3-dimethylphosphorinane, 1,4-dimethylphosphorinane, 8-methyl-8-phosphinobicyclooctane, 4-methyl-4-phosphotetracyclooctane, 1-methylphospholane, 1-methylphosphonane 1,4-diphosphabicyclo[2.2.2]octane, 1,3-dimethylphosphorinane, 1,4-dimethylphosphorinane, 1-methylphosphonane, 1-methylphospholane, 1-methylphosphorinane, 1-phosphabicyclo[2.2.2]octane, 1-phosphabicyclo[2.2.1]-heptane, etc.; and the like.

Among them, preferred are trialkylphosphines having one phosphorus atom in one molecule, such as tri(n-decanyl) phosphine, tri(n-nonyl)phosphine, tri(n-octyl)phosphine, tri (n-heptyl)phosphine, tri(n-hexyl)phosphine, tri(n-pentyl) phosphine, tri(n-butyl)phosphine, tri(n-propyl)phosphine, triethylphosphine, trimethylphosphine, dimethyl(n-octyl) phosphine, di(n-octyl)methylphosphine, dimethyl(n-heptyl) phosphine, di(n-heptyl)imethylphosphine, dimethyl (n-hexyl) phosphine, di (n-hexyl) methylphosphine, etc.

Examples of the dialkylarylphosphine include monophosphines such as dimethylphenylphosphine, diethylphenylphosphine, di(n-propyl)phenylphosphine, di(i-propyl)phenylphosphine, di(n-hexyl)phenylphosphine, di(n-octyl)phenylphosphine, dimethyltolylphosphine, diethyltolylphosphine, di(n-propyl)tolylphosphine, di(i-propyl) tolylphosphine, di(n-hexyl) tolylphosphine, di(n-octyl)tolylphosphine, etc.; polyphosphines such as methylphenylphosphinoethane, ethylphenylphosphinoethane, methylphenylphosphinopropane, etc.; and the like.

With regard to the availability of the above organic phosphines, commercially available phosphines may be generally used but the phosphines can be synthesized according to known methods, if necessary, and used. The synthetic methods for the organic phosphines include Grinard reaction and the like as described in Jikken Kagaku Koza, fourth edition, Vol.24, page 229; H. Hibbert, Chem. Ber., 39, 160 (1906), and so forth, for example. Moreover, a desired organic phosphine may be synthesized by reacting a phosphine having a phenyl group, such as a dialkylphenylphosphine, with lithium metal and further reacting with an alkyl bromide to replace the phenyl group with the alkyl group.

The amount of the organic phosphine to be used is, relative to ruthenium metal, in an atom ratio of phosphorus atom/metal ranging usually from 0.1 to 1000, preferably from 1 to 100. However, in the case of using a compound containing a phosphine where two or more aryl groups are bonded to the phosphorus atom, such as triphenylphosphine, as a ruthenium metal-feeding compound, it is preferable to increase the atom ratio of phosphorus atom/metal so that this-phosphine is replaced with the above organic phosphine.

The characteristic feature of the catalyst for use in the invention is to comprise ruthenium and an organic phosphine wherein aliphatic carbons are bonded to two or more of the three bonding hands of the phosphorus atom as described above, but the catalyst may further comprise a neutral ligand or the like as an optional component.

Examples of the optional component include hydrocarbons having an ethylenic unsaturated bond, such as ethylene, propylene, butene, cyclopentene, cyclohexene, butadiene, cyclopentadiene, cyclooctadiene, norbornadiene, etc.; ethers such as diethyl ether, anisole, dioxane, tetrahydrofuran, etc.; carboxylic acids or carboxylic acid esters such as propionic acid, caproic acid, butyric acid, benzoic acid, methyl benzoate, ethyl acetate, ally acetate, etc.; dimethyl sulfide; organic phosphorus compounds such as tributylphopsphine oxide, ehtyldiphenylphosphine oxide, triphenylphosphine oxide, trioctylphosphine oxide, diethylphenyl phosphinate, diphenylethyl phosphinate, triethyl phosphate, triphenyl phosphite, trioctyl phosphate, hexamethylphosphoric triamide, etc; and further, carbon monoxide, ethylene glycol, carbon disulfide, caprolactam, and the like. Therefore, in some cases, a starting material for the reaction, a reaction product, or a solvent may become a component of the catalyst.

Furthermore, the catalyst may be used in the form of a cationic complex using a conjugate base of an acid whose pKa is less than 2. Preferable results such as the stabilization of the catalyst, the enhancement of the activity, and the like may be obtained by the use of the cationic complex.

As the compound providing the conjugate base of an acid whose pKa is less than 2, a Br$\phi$nsted acid whose pKa is less than 2 or a salt thereof may be usually used. Specific examples include inorganic acids such as nitric acid, perchloric acid, borofluoric acid, hexafluorophosphoric acid, fluorosulfonic acid, etc.; organic acids such as trichloroacetic acid, dichloroacetic acid, trifluoroacetic acid, dodecylsulfonic acid, octadecylsulfonic acid, trifluoromethanesulfonic acid, benzenesulfonic acid, p-toluenesulfonic acid, tetra(pentafluorophenyl)boronic acid, sulfonated styrenedivinylbenzene copolymer, etc.; and alkali metal salts, alkaline earth metal salts, ammonium salts and silver salts of these inorganic acids and organic acids; and the like. Moreover, compounds capable of providing conjugate bases of these acids, such as acid halides, acid anhydrides, esters, acid amides and the like may be also used. These compounds providing conjugate bases of acids whose pKa is less than 2 may be used in an amount of usually 1000 or less moles, preferably 100 or less moles, per mole of ruthenium metal.

In the case of using the catalyst of the invention prepared beforehand, the preparing method is not particularly limited but, as one example, an alcohol solution of a complex compound catalyst is formed by incorporating tris (acetylacetonato)ruthenium and 5 to 20 molar equivalents of a trialkylphosphine into an alcohol of a starting material for reaction and stirring the whole under a hydrogen atmosphere. Moreover, its conversion to a cationic complex can be effected by adding a compound providing a conjugate base of an acid whose pKa is not more than 2 to the solution containing the catalyst obtained in the above, in an amount of 0.1 to 20 moles, preferably 1 to 10 moles, per mole of ruthenium. The cationic complex compound catalyst can be also synthesized by adding, to an alcohol of a starting material for reaction, tris (acetylacetonato) ruthenium, a trialkylphosphine, and a compound providing a conjugate base of an acid whose pKa is not more than 2.

The alcohol of a starting material for reaction may be a monohydric alcohol or a polyhydric alcohol as far as it has primary or secondary hydroxyl group(s). Moreover, the alcohol may be saturated or unsaturated, and may have a substituent. Examples of some monohydric alcohols include methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol, 4-octanol, 1-nonanol, 2-nonanol, 3-nonanol, 4-nonanol, 5-nonanol, 1-decanol, 2-decanol, 3-decanol, 4-decanol, 5-decanol, allyl alcohol, 1-butenol, 2-butenol, 1-pentenol, 2-pentenol, 1-hexenol, 2-hexenol, 3-hexenol, 1-heptenol, 2-heptenol, 3-heptenol, 1-octenol, 2-octenol, 3-octenol, 4-octenol, 1-nonenol, 2-nonenol, 3-nonenol, 4-nonenpl, 1-decenol, 2-decenol, 3-decenol, 4-decenol, 5-decenol, cyclohexanol, cyclopentanol, cycloheptanol, 1-phenythyl alcohol, 2-phenythyl alcohol, methanolamine, ethanolamine, and the like. By the way, in the case of an unsaturated alcohol, the unsaturated bond may be at any position.

Examples of the polyhydric alcohol include dihydric alcohols such as 1,3-propanediol, 1,4-butanediol, 1,5-pentanediol, 1,6-hexanediol, 1,7-heptanediol, 1,8-octanediol, 1,2-cyclohexanedimethanol, 1,3-cyclohexanedimethanol, 1-hydroxymethyl-2-hydroxyethylcyclohexane, 1-hydroxy-2-hydroxypropylcyclohexane, 1-hydroxy-2-hydroxyethylcyclohexane, 1-hydroxymethyl-2-hydroxyethylbenzene, 1-hydroxymethyl-2-hydroxypropylbenzene, 1-hydroxy-2-hydroxyethylbenzene, 1,2-benzylmethylol, 1,3-benzylndimethylol, and the like. When an alcohol having two primary hydroxyl groups is used as a starting material, a polyester may be formed in some cases through intermolecular ester linkage via the reaction process, but in the case that 2 to 4 carbon atoms are present between the carbon atoms to which the primary hydroxyl groups are bonded, a lactone compound can be formed through intramolecular cyclization.

Among the above starting alcohols, preferred are alcohols having 4 or more carbon atoms, and more preferred are diols having 4 or more carbon atoms, such as 1,4-butanediol, 1,5-pentanediol, 1,6-hexanediol, 1,7-heptanediol, 1,8-octanediol, and the like. In particular, the invention is suitable for dehydrogenation and cyclization for producing γ-butyrolactone from 1,4-butanediol.

The hydrogenation of an alcohol according to the invention is carried out usually without solvent, i.e., in the absence of a solvent other than the alcohol of the starting material and a carbonyl compound of the product, but other solvent can be also used, if desired. Examples of the solvent include ethers such as diethyl ether, anisole, tetrahydrofuran, ethylene glycol dimethyl ether, triethylene glycol dimethyl ether, tetraethylene glycol dimethyl ether, dioxane, etc.; alcohols such as methanol, ethanol, n-butanol, benzyl alcohol, ethylene glycol, diethylene glycol, etc.; phenols such as phenol, etc.; carboxylic acids such as formic acid, acetic acid, propionic acid, toluic acid, etc.; esters such as methyl acetate, butyl acetate, benzyl benzoate, etc.; aromatic hydrocarbons such as benzene, toluene, ethylbenzene, L tetralin, etc.; aliphatic hydrocarbons such as n-hexane, n-octane, cyclohexane, etc.; halogenated hydrocarbons such as dichloromethane, trichloroethane, chlorobenzene, etc.; nitro compounds such as nitromethane, nitrobenzene, etc.; carbamides such as N,N-dimethylformamide, N,N-dimethylacetamide, N-methylpyrrolidone, etc.; other amides such as hexamethylphosphoric triamide, etc.; ureas such as N,N-dimethylimidazolidinone, etc.; sulfones such as dimethyl sulfone, etc.; sulfoxides such as dimethyl sulfoxide, etc.; lactones such as γ-butyrolactone, caprolactone, etc.; carbonic acid esters such as dimethyl carbonate, ethylene carbonate, etc.; polyethers such as triglyme, tetraglyme, etc.; and the like.

Among them, preferred are ethers, polyethers, and the like.

The reaction is carried out at the temperature of usually 20 to 350° C., preferably 100 to 250° C., more preferably 150 to 220 C. The catalyst concentration may be in the range wherein industrially desirable activity is shown, but the catalyst may be incorporated into the reaction system in the range of 0.0001 to 100 mol/L, preferably 0.001 to 10 mol/L as ruthenium metal relative to the reaction liquid. The reaction proceeds generally as a homogeneous catalytic reaction.

The catalyst for use in the invention is capable of dehydrogenating an alcohol at a high activity and a high selectivity. Therefore, it is not necessary to incorporate a hydrogen-acceptor in the reaction system but it may be incorporated, if desired. Examples of the hydrogen-acceptor include carbonyl, alkene, or alkyne compounds, such as acetone, diphenylacetylene, vinyl methyl ketone, benzalacetone, ethyl methyl ketone, p-benzoquinone, nitrobenzene, acetonitrile, vinyl chloride, benzonitrile, acetaldehyde, formaldehyde, butyraldehyde, benzaldehyde, etc., or the like.

The reaction pressure may be any pressure as far as the reaction system is maintained a liquid phase, but since the dehydrogenation of an alcohol according to the invention is a hydrogen-forming reaction, it is preferable to carrying out the reaction with removing the hydrogen into outside of the system. Therefore, it is preferred to carry out the reaction in an open system. In the case of carrying out the reaction in a closed system, the atmosphere is preferably an inert gas such as nitrogen, argon, helium, carbon dioxide, or the like. The reaction can be carried out as a batch process or a continuous process. The reaction product solution is subjected to distillation to remove a carbonyl compound formed, and since the catalyst is dissolved in the remaining solution, it is recovered and can be used at next reaction as the catalyst.

The carbonyl compounds, especially lactone compounds obtainable by the method of the invention can be reacted with alkylamines to produce pyrrolidones. For example, N-methylpyrrolidone can be produced by reacting γ-butyrolactone with methylamine and can be industrially used as detergent, solvent, or the like, widely. The production methods for methylamine and N-methylpyrrolidone are not particularly limited and usual methods themselves already known may be adopted. The methods described in U.S. Pat. No. 3,387,032, Japanese Patent Laid-open No. 12514/1997, and so forth may be mentioned as the methods for producing methylamine, but usually, it can be produced by reacting methanol and ammonia in the presence of a catalyst such as silica and/or alumina, zeolite, or the like. As the method for producing N-methylpyrrolidone, for example, method described in Japanese Patent Publication No. 18751/1972 or 78305/1994, and so forth may be used, and the compound can be obtained by reacting mono-, di- and/or trimethylamine with γ-butyrolactone under heating.

Moreover, the carbonyl compounds, especially γ-butyrolactone obtainable by the method of the invention may be used as a solvent for electrolytes as described in Japanese patent Laid-Open No. 97062/1999, 135374/1999, and so forth; a washing solution for polyurethanes as described in Japanese Patent Laid-Open No. 176695/1997 and so forth; and the like.

EXAMPLES

The following will explain the invention more specifically with reference to Examples, but the invention is not limited to following Examples. By the way, the conversion and selectivity were determined by analyzing the reaction solution by gas chromatography using an internal standard method.

Example 1

Into a 500 mL SUS autoclave were introduced tris (acetylacetonato)ruthenium (17.68 g) and 10 molar equivalents of tri(n-octyl)phosphine (162.95 g), and the whole was heated to 190° C. under introducing hydrogen gas at a hydrogen pressure of 0.8 MPa to carry out thermal treatment for 5 hours.

To a 300 mL four-necked flask fitted with a stirrer, a cooler, a temperature-measuring device, and an opening for sampling was added 1,4-butanediol (93.31 g) and the whole was heated to 205° C. The ruthenium catalyst (8.19 g) synthesized by the above preparation method was added thereto, followed by stirring under heating at 203° C. for 6 hours (Ru metal concentration: 2000 ppm by weight). As a result, the conversion of 1,4-butanediol was found to be 99.7 mol % and the selectivity of γ-butyrolactone was found to be 98.0 mol %.

Example 2

The ruthenium catalyst (4.00 g) prepared in Example 1, triglyme (86.80 g) as a solvent, and 1,5-pentanediol (9.39 g) were stirred under heating at 203° C. for 3 hours. As a result, the conversion of 1,5-pentanediol was found to be 100% and the selectivity of valerolactone was found to be 88.9 mol %.

Example 3

Using tri(n-hexyl)phosphine as the ligand, a ruthenium catalyst was prepared by a similar preparation method to Example 1. The catalyst (6.15 g) prepared was added to 1,4-butanediol (93.33 g), which was reacted for 4.5 hours under heating at 203° C. in a similar manner to Example 1 (Ru metal concentration: 2000 ppm by weight). As a result, the conversion of 1,4-butanediol was found to be 100.0 mol % and the selectivity of γ-butyrolactone was found to be 96.6 mol %.

Example 4

Using tri(n-butyl)phosphine as the ligand, a ruthenium catalyst was prepared by a similar preparation method to Example 1. The catalyst (5.19 g) prepared was added to 1,4-butanediol (100.47 g), which was reacted for 4 hours under heating at 203° C. in a similar manner to Example 1 (Ru metal concentration: 2000 ppm by weight). As a result, the conversion of 1,4-butanediol was found to be 100.0 mol % and the selectivity of γ-butyrolactone was found to be 97.0 mol %.

Example 5

The catalyst (2.49 g) in Example 4 was added to 1,4-butanediol (100.31 g), which was reacted for 5 hours under heating at 203° C. in a similar manner to Example 1 (Ru metal concentration: 1000 ppm by weight). As a result, the conversion of 1,4-butanediol was found to be 100.0 mol % and the selectivity of γ-butyrolactone was found to be 98.9 mol %.

Example 6

The catalyst (1.25 g) in Example 4 was added to 1,4-butanediol (99.09 g), which was reacted for 7.5 hours under heating at 203° C. in a similar manner to Example 1 (Ru metal concentration: 500 ppm by weight). As a result, the conversion of 1,4-butanediol was found to be 100.0 mol % and the selectivity was found to be 99.3 mol %.

Example 7

The ruthenium catalyst (2.18 g) prepared in Example 4, triglyme (88.16 g) as a solvent, and 1,5-pentanediol (9.44 g) were stirred under heating at 203° C. for 3 hours. As a result, the conversion of 1,5-pentanediol was found to be 98.6% and the selectivity of valerolactone was found to be 84.5 mol %.

Example 8

Using trimethylphosphine as the ligand, a ruthenium catalyst was prepared by a similar preparation method to Example 1. The catalyst (1.40 g) prepared was added to 1,4-butanediol (43.67 g), which was reacted for 4 hours under heating at 203° C. in a similar manner to Example 1 (Ru metal concentration: 2000 ppm by weight). As a result, the conversion of 1,4-butanediol was found to be 99.8 mol % and the selectivity of γ-butyrolactone was found to be 99.5 mol %.

Example 9

Using tribenzylphosphine as the ligand, a ruthenium catalyst was prepared by a similar preparation method to Example 1. The catalyst (2.56 g) prepared was added to 1,4-butanediol (45.63 g), which was reacted for 6 hours under heating at 203° C. in a similar manner to Example 1 (Ru metal concentration: 2000 ppm by weight). As a result, the conversion of 1,4-butanediol was found to be 99.8 mol % and the selectivity of γ-butyrolactone was found to be 99.2 mol %.

Example 10

Into a 500 mL round flask were placed tris(acetylacetonato)ruthenium (0.32 g), tri(n-octyl)phosphine (3.2 g), triglyme (300 mL), and p-toluenesulfonic acid (2.8 g), and then the whole was heated at 200° C. to carry out thermal treatment for 2 hours.

The catalyst solution was transferred to a 300 mL round flask and 1,4-butanediol (10 g) was added thereto, which was reacted for 4 hours under heating at 200° C. As a result, the conversion of 1,4-butanediol was found to be 100 mol % and the selectivity of γ-butyrolactone was found to be 75.3 mol %.

Example 11

Into a 500 mL SUS autoclave were placed tris(acetylacetonato)ruthenium (0.32 g), trioctylphosphine (3.2 g), and triethylene glycol dimethyl ether (300 mL), and the whole was maintained at 170° C. for 2 hours under pressurizing to 5 MPa with hydrogen to prepare a catalyst solution.

Into a 300 mL round flask were placed the catalyst solution (90 mL) prepared above and 1,4-butanediol (10 g), which was reacted for 4 hours at 200° C. As a result, the conversion of 1,4-butanediol was found to be 99.7% and the selectivity of γ-butyrolactone was found to be 98.0%.

example 12

Into a 300 mL round flask were placed the catalyst solution (45 mL) prepared in Example 11 and 1,4-butanediol (50 g), which was reacted for 6 hours under heating at 200° C. As a result, the conversion of 1,4-butanediol was found to be 99.8 % and the selectivity of γ-butyrolactone was found to be 99.0%.

Example 13

Into a 500 mL SUS autoclave were placed tris(acetylacetonato)ruthenium (0.32 g), trioctylphosphine (3.2 g), and triethylene glycol dimethyl ether (300 mL), and the whole was maintained at 200° C. for 5 hours under pressurizing to 0.8 MPa with hydrogen to prepare a catalyst solution.

Into a 300 mL round flask were placed the catalyst solution (45 mL) prepared above and 1,4-butanediol (50 g), which was reacted for 6 hours under heating at 200° C. As a result, the conversion of 1,4-butanediol was found-to be 99.7% and the selectivity of γ-butyrolactone was found to be 98.0%

Example 14

Using dimethylphosphine as the ligand, a ruthenium catalyst was prepared by a similar preparation method to Comparative Example 1. The catalyst solution (5.81 g) prepared was added to 1,4-butanediol (95.34 g), which was reacted for 7 hours under heating at 203° C. in a similar manner to Example 1 (Ru metal concentration: about 2000 ppm by weight). As a result, the conversion of 1,4-butanediol was found to be 97.8 mol % and the selectivity of γ-butyrolactone was found to be 95.0 mol %.

Comparative Example 1

Using triphenylphosphine as the ligand, a ruthenium catalyst was prepared in toluene solvent by a similar preparation method to Example 1. The catalyst (7.48 g) obtained by removing the toluene by distillation under reduced pressure from the catalyst toluene solution prepared was added to 1,4-butanediol (124.89 g), which was reacted for 8 hours under heating at 203° C. in a similar manner to Example 1 (Ru metal concentration: about 2000 ppm by weight). As a result, the conversion of 1,4-butanediol was found to be 84.0 mol % and the selectivity of γ-butyrolactone was found to be 68.1 mol %.

Comparative Example 2

Using methyldiphenylphosphine as the ligand, a ruthenium catalyst was prepared by a similar preparation method to Comparative Example 1. The catalyst solution (1.94 g) prepared was added to 1,4-butanediol (48.66 g), which was reacted for 12 hours under heating at 203° C. in a similar manner to Example 1 (Ru metal concentration: about 2000 ppm by weight). As a result, the conversion of 1,4-butanediol was found to be 85.0 mol % and the selectivity of γ-butyrolactone was found to be 54.2 mol %.

Comparative Example 3

Using a catalyst preparation method similar to Example 1, an Ir catalyst was synthesized from tris(acetylacetonato)iridium (0.635 g) and 10 molar equivalents of tri(n-octyl)phosphine (4.84 g). The iridium catalyst (3.73 g) was added to 1,4-butanediol (81.5 g) heated at 205° C. similar to Example 1, followed by stirring under heating at 203° C. for 10 hours. As a result, the conversion of 1,4-butanediol was found to be 5.2% and the selectivity of γ-butyrolactone was found to be 0.0 mol %.

Industrial Applicability

According to the method for producing a carbonyl compound by dehydrogenating an alcohol of the invention, the carbonyl compound can be produced industrially advantageously at a good selectivity in high yields under mild reaction conditions.

Furthermore, according to the invention, γ-butyrolactone can be produced industrially advantageously at a good selectivity in high yields under mild reaction conditions by dehydrogenation of 1,4-butanediol and successive cyclization.

What is claimed is:

1. A method for producing a carbonyl compound, comprising:

dehydrogenating an alcohol in the presence of a complex compound catalyst comprising ruthenium and an organic phosphine wherein aliphatic carbons are bonded to two or more of the three bonding hands of the phosphorus atom;

wherein the organic phosphine is a trialkylphosphine.

2. The method according to claim 1, wherein the complex compound catalyst comprises a conjugate base of an acid having a pKa of less than 2.

3. The method according to claim 1, wherein the alcohol is a polyhydric alcohol having two or more primary hydroxyl groups.

4. The method according to claim 1, wherein the carbonyl compound has an ester linkage.

5. The method according to claim 1, wherein the alcohol is 1,4-butanediol and the carbonyl compound is γ-butyrolactone.

6. A method for producing N-methylpyrrolidone, comprising:

reacting γ-butyrolactone obtained by the method according to claim 5 with methylamine.

7. The method according to claim 1, wherein said catalyst further comprises a neutral ligand selected from the group consisting of a hydrocarbon having an ethylenically unsaturated bond, an ether, a carboxylic acid, a carboxylic acid ester, dimethyl sulfide, an organic phosphorous compound, carbon monoxide, ethylene glycol, carbon disulfide and caprolactam.

8. The method according to claim 1, carried out in the absence of a solvent.

9. The method according to claim 1, wherein said dehydrogenating proceeds at a temperature of from 20 to 350° C.

10. The method according to claim 1, wherein a concentration of said catalyst is from 0.0001 to 10 mol/L based on a reaction liquid.

* * * * *